United States Patent

Weinberg et al.

[11] Patent Number: 6,026,325
[45] Date of Patent: Feb. 15, 2000

[54] IMPLANTABLE MEDICAL DEVICE HAVING AN IMPROVED PACKAGING SYSTEM AND METHOD FOR MAKING ELECTRICAL CONNECTIONS

[75] Inventors: Alvin Weinberg, Moorpark; Dion Frank Davis, Palmdale, both of Calif.

[73] Assignee: Pacesetter, Inc., Sylmar, Calif.

[21] Appl. No.: 09/099,164

[22] Filed: Jun. 18, 1998

[51] Int. Cl.[7] .................................................. A61N 1/375
[52] U.S. Cl. ................................ 607/36; 607/9; 29/830; 361/752
[58] Field of Search .................................. 607/36, 2, 1, 9, 607/4, 5; 361/752, 814, 818; 29/830; 257/685, 686, 668, 723, 724, 730, 777; 439/526, 909

[56] References Cited

U.S. PATENT DOCUMENTS

| | | | |
|---|---|---|---|
| 4,127,134 | 11/1978 | Ushakoff | 128/419 |
| 4,254,775 | 3/1981 | Langer | 128/419 |
| 4,370,700 | 1/1983 | Duddles et al. | 361/424 |
| 4,616,655 | 10/1986 | Weinberg et al. | 128/419 |
| 4,744,009 | 5/1988 | Grabbe et al. | 361/398 |
| 4,890,623 | 1/1990 | Cook et al. | 128/642 |
| 4,967,755 | 11/1990 | Pohndorf | 128/675 |
| 4,995,389 | 2/1991 | Harris | 128/419 |
| 5,051,869 | 9/1991 | Goldfarb | 361/399 |
| 5,090,422 | 2/1992 | Dahl et al. | 128/784 |
| 5,103,818 | 4/1992 | Maston | 128/419 |
| 5,131,388 | 7/1992 | Pless et al. | 128/419 |
| 5,156,151 | 10/1992 | Imran | 128/642 |
| 5,241,957 | 9/1993 | Camps et al. | 607/119 |
| 5,275,171 | 1/1994 | Barcel | 607/122 |
| 5,282,841 | 2/1994 | Szyszkowski | 607/36 |
| 5,336,246 | 8/1994 | Dantanarayana | 607/37 |
| 5,406,946 | 4/1995 | Imran | 128/642 |
| 5,408,383 | 4/1995 | Nagasaka et al. | 361/752 |
| 5,415,166 | 5/1995 | Imran | 128/642 |
| 5,438,987 | 8/1995 | Thacker et al. | 128/634 |
| 5,454,160 | 10/1995 | Nickel | 29/840 |
| 5,521,786 | 5/1996 | Gochi et al. | 361/752 |
| 5,610,799 | 3/1997 | Kato | 361/752 |
| 5,741,313 | 4/1998 | Davis et al. | 607/36 |
| 5,800,650 | 9/1998 | Anderson et al. | 29/830 |
| 5,835,350 | 11/1998 | Stevens | 361/752 |

FOREIGN PATENT DOCUMENTS

| | | |
|---|---|---|
| 55-61046 | 5/1980 | Japan . |
| 59-44851 | 3/1984 | Japan . |
| 59-44852 | 3/1984 | Japan . |
| 60-10764 | 1/1985 | Japan . |
| 60-117763 | 6/1985 | Japan . |
| 1-28855 | 1/1989 | Japan . |
| 1-147850 | 6/1989 | Japan . |
| 2241895 | 9/1991 | United Kingdom . |

*Primary Examiner*—Kennedy J. Schaetzle

[57] ABSTRACT

An implantable cardiac stimulation device having an improved multi-level electronic package is disclosed. The multi-lever package includes at least two stacked internal substrates for mounting electronic circuits, a protective lid for protecting the substrates, and an external interconnect structure mounted on the lid which is also capable of mounting electronic components. The interconnection between the at least two internal substrates is achieved by vertically-oriented wirebonds, and the interconnection between at least one internal substrate and the external interconnect structure is achieved by vertically-oriented brazed-on pins which pass through holes in the protective lid. This construction minimizes the planar dimensions of the electronic package and optimizes space in the physiologically-curved portions of the housing.

7 Claims, 3 Drawing Sheets

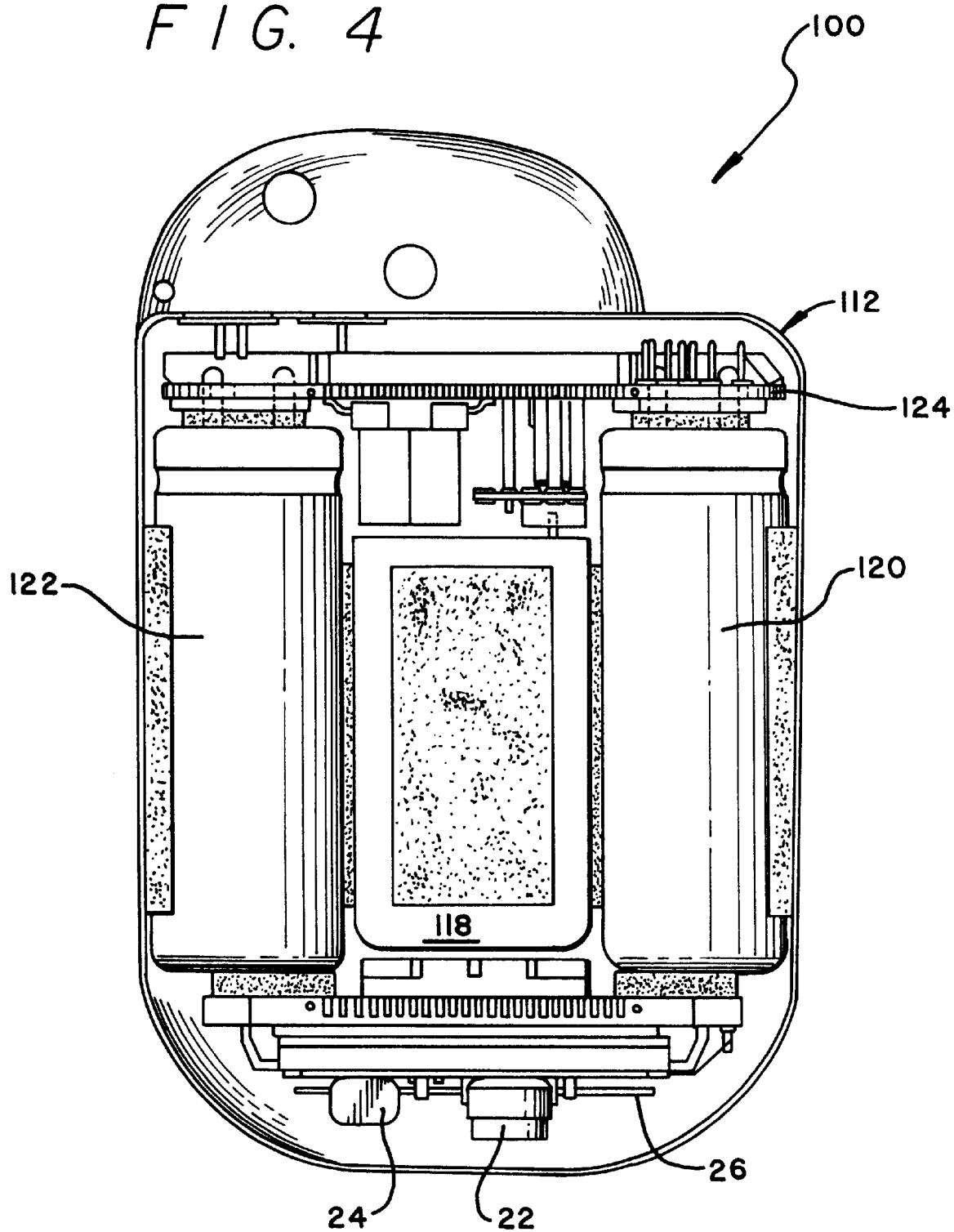

IMPLANTABLE MEDICAL DEVICE HAVING AN IMPROVED PACKAGING SYSTEM AND METHOD FOR MAKING ELECTRICAL CONNECTIONS

FIELD OF THE INVENTION

This invention relates generally to improvements in the packaging of electronic components suitable for implantable medical devices, and more particularly, to providing a multi-level high density electrical package which is developed vertically rather than horizontally to optimize space in a physiologically-shaped implantable housing.

BACKGROUND OF THE INVENTION

It will be appreciated that the invention has applications with respect to improvements in electronic packaging may be suitable for many applications. However, the present invention has some unique features which maximize utilization of space within an implantable medical device.

Implantable medical devices of the type having electrical circuit components are well known in the medical arts. In one particularly common form, the implantable device comprises a pacemaker having an appropriate electrical power supply and related control circuitry for use in electrically stimulating a patient muscle, such as the heart. Such a pacemaker commonly includes an hermetically sealed case or housing within which the power supply and control circuitry are protectively encased, in combination with one or more conductive pacemaker leads extending from the housing to the selected muscle structure within the patient.

Signals into and out of the circuitry within the housing are coupled through the housing by means of feedthrough terminals of various types known in the art. Examples of such a cardiac pacemaker may be found in commonly assigned U.S. Pat. No. 5,282,841 to Szyszkowski.

As is apparent from the Szyszkowski patent, the size of the housing is dependent upon that required to house both the battery and the electronic circuit constituting the pulse generator. A major factor which drives the electronic package design is the need to fit large, generally rectangular or cylindrical components into a physiologically-shaped, curved housing. Of course, efforts are continually being made to minimize the size of the housing while maximizing the effectiveness of the device. To a large extent the size of the battery is dependent upon the anticipated lifetime, as well as cost factors of the type of battery employed. In addition to improvements in batteries, great strides have been made in component packaging which greatly affects the size of the electronic circuit employed. For example, the circuitry illustrated in the U.S. Pat. No. 4,127,134 to Ushakoff shows discrete components as opposed to integrated circuits or chips as employed, more recently, in the U.S. Pat. No. 4,616,655 to Weinberg et al. The Weinberg et al. patent discloses a microprocessor based pulse generator for use as a cardiac pacemaker and utilizes integrated circuits including active chips, such as microprocessors and other active circuits, together with passive chips, such as chip resistors and chip capacitors. The use of such integrated circuits requires less space than discrete components and, thus, provides a reduction in the size necessary for the circuitry employed in such an implantable pulse generator.

As disclosed in Weinberg et al., the pulse generator includes an implantable sealed housing of biocompatible material and which contains a power supply and a pulse generator circuit powered by the supply for providing stimulation pulses. The electronic pulse generator circuit includes a plurality of semiconductor chips including active chips and passive chips together with chip carrier means for carrying the semiconductor chips in a single structure. The active chips are mounted in a hermetically sealed cavity located in one of the major surfaces of the assembly and the passive chips are mounted to bonding pads located on the other major surface. The passive chips and active chips are electrically interconnected by way of a network of metallized paths located on the various ceramic layers together with vertically extending electrically conductive vias which extend through various of the layers to the passive chip mounting pads. Various of these metallized paths also extend laterally outward to metallized edges which extend along the peripheral edge of the assembly to I/O mounting pads on the bottom surface of the assembly so that the assembly may be electrically and physically mounted to a mother board or a substrate.

The present invention represents a continuation of the improvements begun by Weinberg at al. and it was in light of the foregoing that the present invention was conceived and has now been reduced to practice.

SUMMARY OF THE INVENTION

The present invention comprises a multi-level electronic package having at least two stacked internal substrates for mounting electronic circuits, a protective lid for protecting the substrates, and an external interconnect structure mounted on the lid which is also capable of mounting electronic components. The interconnection between the at least two internal substrates is achieved by vertically-oriented wirebonds, and the interconnection between at least one internal substrate and the external interconnect structure is achieved by vertically-oriented brazed-on pins which pass through holes in the protective lid.

More specifically, the present invention comprises a hybrid assembly including a first substrate having a cavity on a first side which defines a depressed surface for supporting electronic circuitry including passive and active components and their electrical interconnections.

The present invention further includes an intermediate substrate mounted on the first side of the first substrate, the intermediate substrate having a lower surface facing the depressed surface and an upper surface. Both surfaces of the intermediate substrate are capable of supporting electronic circuitry including active and passive components and their electrical interconnections.

Advantageously, vertically-oriented wirebonds form the interconnection between the first and intermediate substrate to optimize packing density.

A lid is used to protect the active components on the first and intermediate substrates. The lid is further capable of supporting and interconnecting the large, typically externally-mounted pacemaker components (such as inductors, telemetry coils, and a reed switch) to the hybrid assembly.

The lid is mounted on the first side of the first substrate overlying the upper surface of the intermediate substrate and has a plurality of holes therein. Advantageously, up-standing pin terminals are mounted on the upper surface of the intermediate substrate which are slidably received through holes on the lid. The up-standing pins provide vertical connection between the specific electronic components on the intermediate substrate and the externally-mounted components.

While the embodiment described above includes an external interconnect structure, it is within the spirit of the invention to mount the external pacemaker components directly onto the lid.

Advantageously, the hybrid assembly is dimensioned and oriented so that the large pacemaker components may be positioned on the external interconnect structure so as to fit in the curved portion of the pacemaker housing. In this way, space utilization is high regardless of the particular curved-shape of the pacemaker housing.

This vertically-oriented construction and the dimensioning to fit in the curved portion of the pacemaker housing significantly minimizes the overall dimensions of the electronic package which makes it ideally suitable for an implantable stimulation device.

Accordingly, a primary feature of the present invention is to provide improvements in the packaging of electronic components and their circuitry.

Another feature of the invention is to provide a multi-level high density electronic package which is caused to develop vertically rather than horizontally.

A further feature of the invention is to provide a high density electronic package for an implantable medical device which is of minimal size but of maximized effectiveness.

Still another feature of the present invention is to provide a multi-level, high density package which makes direct electrical connection among the external components and the hybrid substrate by providing pin terminals which exit through the hybrid lid and is vertically-registered to an externally mounted rigid flex circuit or similar substrate which mounts the external components thereon.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 4 is a plan view of a cardiac stimulation device depicting the configuration of the assembled internal components in accordance with a preferred embodiment.

DETAILED DESCRIPTION OF THE PREFERRED EMBODIMENTS

Figure 1:
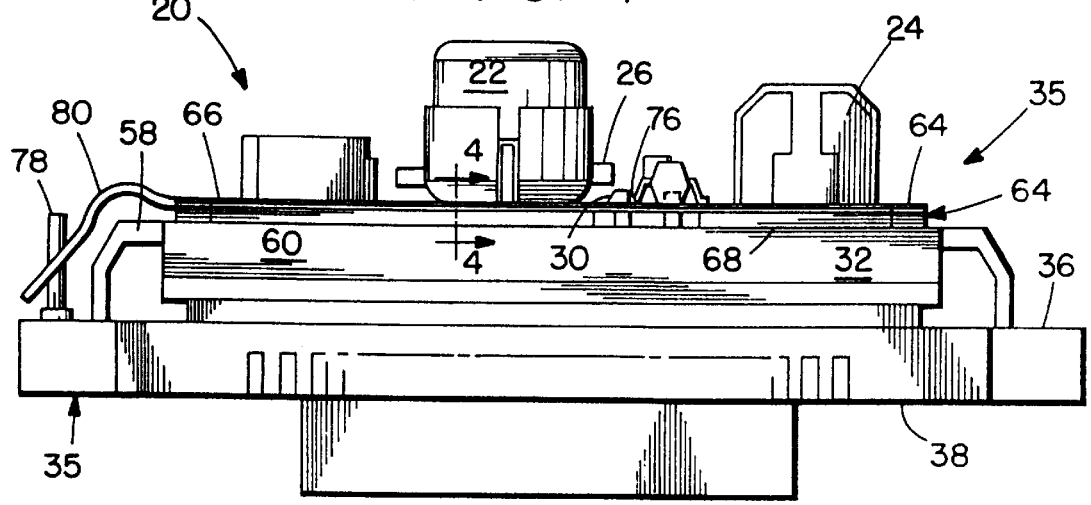
FIG. 1 is a side elevation view of a high density electronic package embodying the invention.
Figure 2:
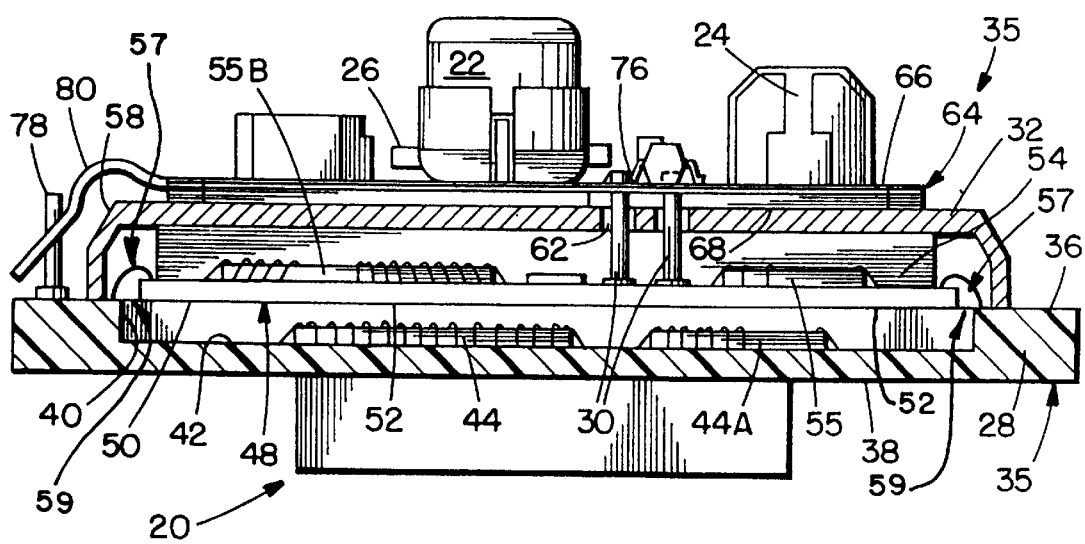
FIG. 2 is a is a side elevation view, in section, of the high density electronic package illustrated in FIG. 1.
Figure 3:
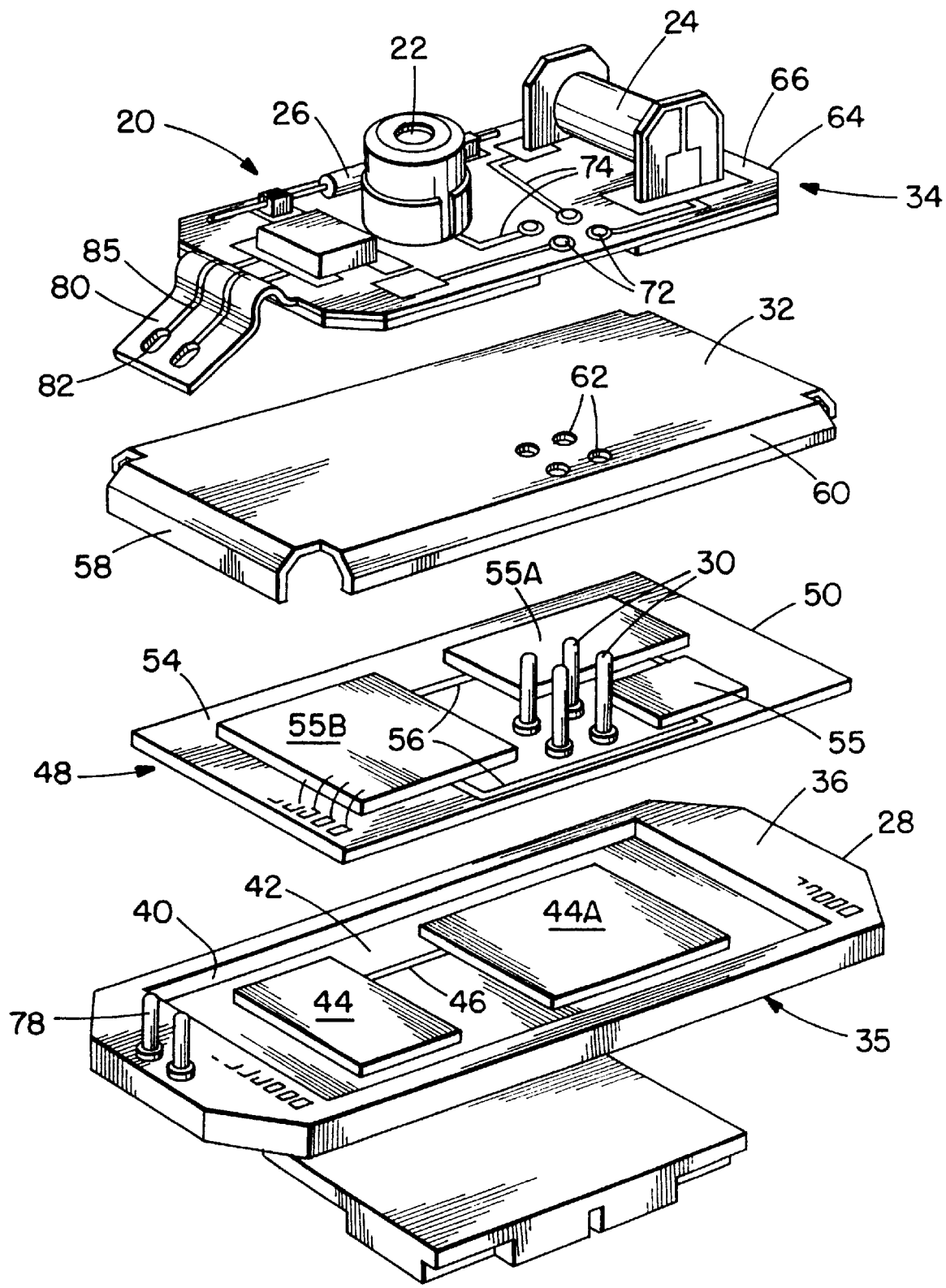
FIG. 3 is an exploded perspective view of the high density electronic package illustrated in FIGS. 1 and 2.

Turn now to the drawings and, initially, to FIGS. 1, 2, and 3 which illustrate a multi-level high density electronic package 20 embodying the present invention. The invention has particular application for implantable medical devices such as pacemakers and defibrillators, but the technology presented in this disclosure can be used in any instance in which space is at a premium in electronic devices. Thus, for example, considering the invention to be applied to a pacemaker, as the number of components increase, and packaging density becomes more complex, finding real estate and space for mounting the "external" pacing components (e.g., the inductor 22, the telemetry coil 24, and the reed switch 26) becomes a critical problem.

In order to solve the problem, the present invention provides a multi-level, high density package 20 which makes direct electrical connection among such external components 22, 24, and 26 and a first substrate 28 by providing a plurality of pin terminals 30 which exit through a hybrid lid 32 to an externally mounted interconnect structure 34 (e.g., a printed circuit board, a flexible circuit, a rigid flexible circuit, a ceramic, thick film, or other hybrid substrate), which mounts the external components thereon.

More specifically now, and with continuing reference to the drawings, the high density electronic package 20 is seen to include a first hybrid assembly 35 including the first substrate 28 having first and second opposed surfaces 36, 38, respectively, and a cavity 40 formed into the first opposed surface defining a depressed surface 42 and electronic circuitry mounted on the first substrate including components 44, 44A, such as integrated circuits and electrical interconnections 46 thereamong. The electronic package 20 further comprises an intermediate hybrid assembly 48 including an intermediate substrate 50 mounted on the first opposed surface 36 of the first substrate 28. The intermediate substrate has a lower surface 52 facing the depressed surface 42 of the first substrate and an upper surface 54 facing away from the depressed surface. As with the first substrate 28, electronic circuitry on the intermediate substrate 50 includes electronic components 55, 55A, 55B and electrical interconnections 56 among the components.

The interconnection between the first substrate 28 and the intermediate substrate 50 is achieved by wirebonds 57 (FIG. 1) which are in vertical registration between a plurality of wirebond pads 41 on the first substrate 28 and a plurality of wirebond pads 51 on the intermediate substrate 50 (FIG. 3). Advantageously, the vertically-oriented wirebonds between substrates significantly optimizes packing density.

As earlier noted, a plurality of upstanding pin terminals 30 are mounted, as by brazing, on the upper surface 54 of the intermediate substrate 50. The pin terminals 30 have electrical continuity with specific ones of the electronic components 55 mounted on the intermediate substrate 50 by means of internal tracing or vias (not shown) within the substrate 50.

The location of the pin terminals was optimized for performance for the particular application. That is, for high-speed connections or sensitive nodes, the most direct interconnection is preferred. In the present invention, the solution was to provide a vertical interconnect through the lid. Not only did this provide the most direct interconnect, but the brazed pins advantageously added rigid structure to the whole assembly.

While the dimensions of the intermediate substrate 50 is generally similar to that of the first substrate 28, the intermediate substrate 50 may be shorter on one or two opposing sides of the cavity 40 resulting in an opening 59 between the exterior of the electronic package 20 and the cavity 40. The opening 59 of the package enables vapor deposition of a suitable polymer coating (e.g., parylene) for protection of the electronic components and features within the cavity, if desired.

The hybrid lid 32, mentioned above, includes a pair of opposed laterally extending legs 58 and a pair of opposed longitudinally extending legs 60 for mounting it, respectively, on the first surface 36 of the first substrate 28 and on the upper surface 54 of the intermediate substrate 50 so as to be spaced from and overlying the upper surface 54 of the intermediate substrate 50 and the electronic components mounted on that upper surface. The lid 32 is suitably formed with a plurality of holes 62 therein (FIGS. 2 and 3) for slidably receiving the upstanding pin terminals so that they extend through and beyond the holes.

An outer substrate 64 has outer and inner opposed surfaces, 66, 68, respectively, and is suitably mounted on the lid, as by adhesive 70. The outer substrate 64 has a plurality of holes 72 formed therein, for vertically registry with the holes 62 in the lid 32, also for the slidable reception therethrough of the upstanding pin terminals 30. The outer substrate 64 supports electronic circuitry on its upper surface 64 comprised of electronic components such as the inductor 22, the telemetry coil 24, and the reed switch 26 as well as electrical tracing 74 adjacent the holes 72 and suitable interconnections 76 joining each of the pin terminals 30 with the electrical tracing 66 adjacent the particular hole through which each of the pin terminals extends. Advantageously, these electronic components 22, 24, 26 may be mounted in such a manner that they fit (heightwise) in the curved portion of the pacemaker housing, thereby maximizing the utilization of space in the pacemaker. In this manner, the components 55, 55A, 55B on the intermediate hybrid assembly 48 are electrically connected with the components 22, 24, 26, and others, as desired, on the outer substrate 64 on the lid 32.

Advantageously, with the use of the upstanding pin terminals 30, the planar dimensions, that is, in lateral and longitudinal directions, of the electronic package 20 are minimized with some, but relatively minimal, increase in the vertical direction.

With continuing reference to FIG. 3, it is seen that a plurality of upstanding supplemental pin terminals 78 are mounted on the first surface 36 of the first substrate 28 which have electrical continuity with specific electronic components mounted on the first substrate. Such electrical continuity is achieved by means of electrical tracing or vias (not shown) within the substrate. The outer substrate 64 may include a flexible portion 80 with through holes 82 therein located for the slidable reception therethrough of the upstanding supplemental pin terminals 78 when the flexible portion is deformed toward the first substrate. Substrate 64 is of the rigid-flex variety, whereby a number of rigid and flexible circuit layers can be laminated together, thereby creating a substrate engineered with certain regions flexible, and others rigid. Interconnections may be achieved in any suitable manner, as by solder reflowed about each of the supplemental pin terminals 78 to thereby join the pin terminals with electrical tracing 85 adjacent the appropriate hole 82 through which each of the supplemental pin terminals extends. In this manner, the components on the first hybrid assembly 35 are thereby electrically connected with the components on the interconnect structure 34.

In the context of an implantable medical device, such as a pacemaker or defibrillator, the intermediate hybrid assembly 48 may be a digital hybrid assembly and the first hybrid assembly 35 may be an analog hybrid assembly.

FIG. 4 shows one embodiment of the present invention within an implantable cardioverter defibrillator (ICD). For a complete description of the ICD, see U.S. Pat. No. 5,471, 313, which patent is hereby incorporated by reference in its entirety.

Briefly, an internal view of the ICD device 100 is shown in final assembled form. The electronic package 20 is advantageously optimized to reduce the required volume of the housing 112.

Housed within the housing 112 are internal components including a battery 118, charge capacitors 120 and 122, a high-voltage electronics package 124, and the electronics package 20.

The electronics package 20 is shown in the lower curved portion of the housing. The electronics package 20 is a control module which performs cardiac pacing and sensing functions for determining when a high voltage discharge is warranted. The basic design and operation of a typical cardioverter-defibrillator are common to one of ordinary skill in the art and will not be discussed in detail in accordance with a preferred embodiment of the present invention.

The other internal components of the ICD device 100, including the battery 118, the capacitors 120 and 122, and the modules 124 and 126, are uniquely configured within the housing 112 to optimize available space. The rounded periphery of the housing 112 creates substantially semi-circular lower portion. Components 22, 24 and 26 on the electronics package 20 are advantageously placed within these substantially semi-circular internal portions of the housing 112.

Advantageously, the hybrid assembly is dimensioned and oriented so that the large external pacemaker components may be positioned on the external interconnect structure so as to fit in the curved portion of the pacemaker housing. In this way, space utilization is high regardless of the particular curved-shape of the pacemaker housing.

This vertically-oriented construction and the dimensioning to fit in the curved portion of the pacemaker housing significantly minimizes the overall dimensions of the electronic package which makes it ideally suitable for an implantable stimulation device.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable cardiac stimulation device for stimulating a patient's heart, comprising:

a housing for implantation in the human body, the housing having a predetermined thickness;

a multi-level high density electronic module, including pulse generator circuitry, having a width that matches the width of the housing, the electronic module having a plurality of vertically-registered substrates, the substrates including:

a first substrate having a cavity formed therein for mounting electronic circuitry including components and electrical interconnections therebetween;

an intermediate substrate, mounted in vertical registration above the first substrate, for mounting electronic circuitry including components and electrical interconnections therebetween, the intermediate substrate having vertically-oriented wirebonds for electrically connecting the components on the first substrate to the components on the intermediate substrate;

at least one up-standing pin terminal, mounted on the intermediate substrate, which has electrical continuity with specific ones of the components mounted on the intermediate substrate; and a lid, mounted on the first substrate and the overlying intermediate substrate, having at least one hole in vertical registration with the up-standing pin terminal for slidable reception therethrough, the lid including electronic circuitry comprised of components and electrical interconnections to join the at least one pin terminal with the components on the lid;

thereby minimizing the overall thickness of the housing and providing mechanical strength to the electronic module.

2. The implantable cardiac stimulation device, as set forth in claim 1, wherein:

the housing has a physiologically-curved lower portion; and the electronic module is oriented so that the components mounted on the lid fit within the curved portion of the housing.

3. The implantable cardiac stimulation device, as set forth in claim 1, wherein the electronic circuitry on the lid is directly mounted onto the lid.

4. The implantable cardiac stimulation device, as set forth in claim 1, wherein the electronic circuitry on the lid comprises:

an external substrate, mounted on the lid, having a plurality of holes therein for the slidable reception therethrough of the at least one up-standing pin terminal and electronic circuitry comprised of components and electrical tracings adjacent the holes therein to thereby electrically connect the components on the intermediate substrate assembly with the components on the external substrate; and adhesive means for mounting the external substrate on the lid.

5. The implantable cardiac stimulation device, as set forth in claim 4, wherein the external substrate comprises a rigid-flexible circuit.

6. The implantable cardiac stimulation device, as set forth in claim 5, further comprising:

at least one up-standing supplemental pin terminal mounted on the first substrate which has electrical continuity with specific ones of the electronic components mounted on the first substrate; and wherein the external substrate includes an integral flexible portion with through-holes therein located for the slidable reception therethrough of the at least one up-standing supplemental pin terminal when deformed toward the first substrate, and further having interconnections for joining the at least one supplemental pin terminal with the components on the external substrate.

7. A method of making electrical connections in an implantable cardiac stimulation device, comprising the steps of:

providing a housing having a predetermined thickness suitable for implantation in the body;

providing a first substrate having a cavity formed therein for mounting electronic circuitry including components and electrical interconnections therebetween, the first substrate having a width that matches the width of the housing;

mounting an intermediate substrate, for mounting electronic circuitry including components and electrical interconnections therebetween, in vertical registration above the first substrate;

vertically-orienting wirebonds between the first substrate and the intermediate substrate for electrically interconnecting the components therebetween;

mounting at least one up-standing pin terminal on the intermediate substrate, the pin terminal having electrical continuity with specific ones of the components mounted on the intermediate substrate;

mounting a lid on the first substrate and overlying the intermediate substrate, having at least one hole in vertical registration with the up-standing pin terminal for slidable reception therethrough, the lid including electronic circuitry comprised of components and electrical interconnections; and joining the at least one pin terminal with the electrical interconnection on the lid to thereby electrically connect components on the intermediate substrate with components on the lid, the at least one pin terminal providing both a direct electrical interconnect and a mechanical support structure;

thereby minimizing the overall thickness of the housing and providing mechanical strength to the electronic module.

* * * * *